United States Patent [19]

Lafon

[11] Patent Number: 4,816,489
[45] Date of Patent: Mar. 28, 1989

[54] 1-(AMINOPHENYL)-2-AMINOETHANONE DERIVATIVES

[75] Inventor: Louis Lafon, Paris, France

[73] Assignee: Laboratoire L. Lafon, Alfort, France

[21] Appl. No.: 95,348

[22] Filed: Sep. 10, 1987

Related U.S. Application Data

[63] Continuation of Ser. No. 767,135, Aug. 19, 1985, abandoned.

[51] Int. Cl.$^4$ .................. A61K 31/135; C07C 95/08; C07C 97/10
[52] U.S. Cl. .................. 514/649; 514/554; 564/342; 564/343; 564/345
[58] Field of Search .................. 564/342, 343, 345; 514/554, 649

[56] References Cited

U.S. PATENT DOCUMENTS

| | | | |
|---|---|---|---|
| 2,128,255 | 8/1938 | Krzikalla et al. | 564/342 X |
| 2,151,518 | 3/1939 | Krzikalla et al. | 564/342 X |
| 3,082,255 | 3/1963 | Stevens et al. | 564/342 |
| 3,151,124 | 9/1964 | Huebner | 564/342 X |
| 3,171,858 | 3/1965 | L'Italien | 564/342 |
| 3,225,096 | 12/1965 | Mills et al. | 564/342 X |
| 3,313,687 | 4/1967 | Siemer | 564/342 X |
| 3,344,188 | 9/1967 | Wollweber et al. | 564/363 |
| 3,492,351 | 1/1970 | Koppe et al. | 564/343 X |
| 3,819,706 | 6/1974 | Mehta | 564/343 X |
| 4,063,025 | 12/1977 | Murakami et al. | 564/345 X |

FOREIGN PATENT DOCUMENTS

| | | | |
|---|---|---|---|
| 56-90044 | 7/1981 | Japan | 564/342 |
| 175266 | 5/1961 | Switzerland | 564/343 |
| 175267 | 5/1961 | Switzerland | 564/343 |

*Primary Examiner*—Robert V. Hines
*Attorney, Agent, or Firm*—Pigott & Gerstman, Ltd.

[57] ABSTRACT

The present invention relates to the preparation of new derivatives selected from the group consisting of:
(i) 1-(aminophenyl)-2-(alkylamino)ethanones of the formula:

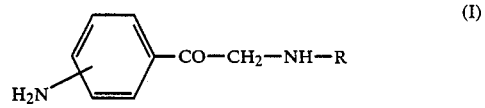

(I)

in which R is $CH(CH_3)_2$ or $C(CH_3)_3$; and
(ii) addition salts thereof.

These new derivatives are useful in therapy, in particular as antidepressants or stimulants for the CNS. They are prepared from 1-(acetylaminophenyl)-2-(alkylamino)ethanone derivatives by deacetylation.

8 Claims, No Drawings

1-(AMINOPHENYL)-2-AMINOETHANONE DERIVATIVES

The present invention relates to 1-(aminophenyl)-2-aminoethanone derivatives by way of new industrial products. It also relates to the method for the preparation of these new products and to their use in therapy, in particular as antidepressants for the central nervous system (abbreviated to CNS).

The new derivatives according to the invention are selected from the group consisting of:

(i) the 1-(aminophenyl)-2-(alkylamino)ethanones of the formula:

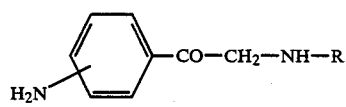
(I)

in which R is $CH(CH_3)_2$ or $C(CH_3)_3$; and (ii) addition salts thereof.

Addition salts are understood here as meaning, on the one hand, the acid addition salts obtained by reacting a free base of the formula I with a mineral or organic acid, and, on the other hand, the ammonium salts. Among the acids which can be used to form salts with the free bases of the formula I, hydrochloric, hydrobromic, acetic, formic, propionic, oxalic, fumaric, maleic, succinic, benzoic, cinnamic, mandelic, citric, malic, tartaric, aspartic, glutamic, methanesulfonic and p-toluenesulfonic acids may be mentioned in particular. Among the compounds making it possible to obtain ammonium salts, $CH_3I$ and $CH_3Cl$ may be mentioned in particular. In general, the acid addition salts are preferred to the ammonium salts.

Taking account of the definitions given above, the $NH_2$ group attached to the benzene nucleus can be in the ortho, meta or (preferably) para position. The group R is preferably the isopropyl group.

A few typical compounds according to the invention have been collated in Table I below without in any way implying a limitation. The most valuable compounds consist of 1-(4-aminophenyl)-2-isopropylaminoethanone and acid addition salts thereof, in particular the dihydrochloride.

TABLE I

| | A—CO—CH₂—NH—R | | |
|---|---|---|---|
| Product | Code no. | A | R |
| Ex. 1(a) | — | 4-aminophenyl | $CH(CH_3)_2$ |
| Ex. 2(b) | CRL 41 121 | 4-aminophenyl | $CH(CH_3)_2$ |
| Ex. 3(c) | — | 3-aminophenyl | $CH(CH_3)_2$ |
| Ex. 4(b) | — | 2-aminophenyl | $C(CH_3)_3$ |
| Ex. 5(b) | — | 4-aminophenyl | $C(CH_3)_3$ |
| Ex. 6(b) | — | 3-aminophenyl | $C(CH_3)_3$ |

Notes
(a) free base
(b) dihydrochloride
(c) dimethanesulfonate

A compound of the formula I can be prepared using a method known per se by the application of classical reaction mechanisms. The method of preparation which is recommended according to the invention consists in subjecting an acetanilide of the formula:

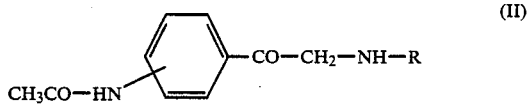
(II)

(in which R is defined as indicated above) to a deacetylation reaction with a concentrated acid, at the reflux temperature of the reaction medium, for at least 0.25 hour.

The compounds according to the invention have valuable therapeutic properties towards the CNS due to the antidepressant and stimulant effects which they exhibit. Their neuropsychopharmacological profile makes them similar to the amphetamines. However, they differ from the said amphetamines by the absence of particular toxicity towards grouped mice; for this, see the results of the tests relating to CRL 41 121 (product of Example 2) below.

According to the invention, a therapeutic composition is recommended which contains, in association with a physiologically acceptable excipient, a derivative selected from the group consisting of (i) the 1-(aminophenyl)-2-(alkylamino)ethanones of the formula I and non-toxic addition salts thereof, and (ii) mixtures thereof, as the active principle.

Of course, in a composition of this type, the active principle is present in a pharmaceutically effective quantity.

Further advantages and characteristics of the invention will be understood more clearly on reading the following description of preparative examples on the one hand and results of pharmacological tests on the other; these data as a whole do not imply a limitation but are given by way of illustration.

PREPARATION I

Preparation of 1-(4-aminophenyl)-2-isopropylaminoethanone dihydrochloride

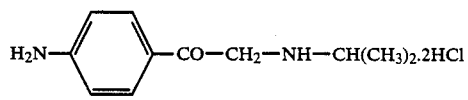

(Example 2; code no.: CRL 41 121)

20 g of 1-(4-acetylaminophenyl)-2-isopropylaminoethanone hydrochloride are dissolved in 200 ml of 4N HCl and the reaction medium is heated under reflux for 0.25 hour. After evaporation of ⅔ in vacuo, the expected dehydrochloride crystallizes in the form of light yellow flakes. After the precipitate has been filtered off, washed with iced water and then dried, 17 g (yield: 74%) of CRL 41 121 are obtained. M.p. (inst.)=about 260° C.

PREPARATION II

Preparation of 1-(4-aminophenyl)-2-isopropylaminoethanone (Example 1)

The free base (m.p. (inst.)=114° C.) is obtained from the corresponding dihydrochloride (CRL 41 121) by saponification.

The results of the tests which were undertaken with CRL 41 121 (product of Example 2), which is the preferred compound according to the invention from the therapeutic point of view, have been summarized below. In these tests, CRL 41 121, in solution in distilled water (at a pH of the order of 2-3), was administered intraperitoneally in a volume of 20 ml/kg to male mice and 5 ml/kg to male rats, unless stated otherwise. The pH varies according to the concentration and in particular is 2.5 for a concentration of 1.6 g/l (dose of 32 mg/kg) and 3 for a concentration of 0.8 g/l (dose of 16 mg/kg).

I. TOXICITY

In male mice, the $LD_0$(maximum non-lethal dose) by intraperitoneal administration is greater than 128 mg/kg and the $LD_{100}$ is less than or equal to 256 mg/kg.

II. OVERALL BEHAVIOR AND REACTIVITIES

Groups of three animals are observed before and then 0.25 hour, 0.50 hour, 1 hour, 2 hours, 3 hours and 24 hours after the administration of CRL 41 121. The following observations are made:

(1°) in mice
at doses of 1 mg/kg and 4 mg/kg:
no particular symptoms:
at a dose of 16 mg/kg:
excitation (0.5 to 3 hours),
an increase in the fear reaction (2 hours), and
an increase in the reactivity to touch (3 hours); and
at a dose of 64 mg/kg:
excitation (0.5 hour to 3 hours),
an increase in the fear reaction,
an increase in the reactivity to touch of 1 hour (3 out of 3 animals) to 3 hours (2 out of 3 animals), and
slight hypothermia (of −2.2° C. for 2 out of 3 animals) 0.5 hour after administration;
(2°) in rats
at doses of 0.5 mg/kg and 2 mg/kg:
no particular symptoms;
at a dose of 8 mg/kg:
an increase in the aggresiveness,
an increase in the reactivity to touch, and
mydriasis 0.5 hour after administration; and
at a dose of 32 mg/kg:
excitation (0.25 hour to 2 hours),
stereotypies (0.5 hour to 2 hours),
stimulation of the respiration,
an increase in the fear reaction (0.25 hour to 2 hours),
an increase in the reactivity to touch (0.50 hour to 2 hours),
slight hyperthermia (+1.4° C.) for 2 hours, and
mydriasis lasting for 2 hours and at a maximum 0.5 hour after administration.

III. ACTION OF THE TEMPERATURE

Groups of 12 mice receive CRL 41 121 and the rectal temperature is noted every 30 minutes.

At doses of 16 mg/kg, 32 mg/kg and 64 mg/kg, it is found that CRL 41 121 causes slight hypothermia which is at a maximum after 30 minutes and disappears after 60 minutes. At a higher dose (128 mg/kg), no hypothermia is observed.

IV. INVESTIGATION OF STEREOTYPE MOVEMENTS

Groups of 6 rats receive an intraperitoneal injection of CRL 41 121 or distilled water immediately before being placed in small cages, where their stereotype behavior is noted every 10 minutes until the effect wears off.

It is observed that CRL 41 121 causes the appearance of stereotype movements in rats as from a dose of 8 mg/kg. The intensity of this effect increases with the dose and, at 16 mg/kg, reaches a level comparable to that obtained with 2 mg/kg of amphetamine.

V. INTERACTION WITH APOMORPHINE (1°) In mice

Groups of 6 mice receive CRL 41 121 0.5 hour before the subcutaneous injection of 1 mg/kg or 16 mg/kg of apomorphine. It is observed that CRL 41 121 causes discreet hypothermia at the strongest dose used (64 mg/kg) and antagonizes (16 mg/kg and 64 mg/kg) the hypothermia induced by apomorphine in mice, without modifying the righting attitude and the stereotypies.

(2°) In rats

CRL 41 121 is administered to groups of 6 rats 0.5 hour before the subcutaneous injection of 0.5 mg/kg of apomorphine. It is observed that, at doses of 8 mg/kg and especially 32 mg/kg, CRL 41 121 causes an increase in the index of the stereotypies induced by apomorphine in rats.

VI. INTERACTION WITH AMPHETAMINE

Amphetamine (2 mg/kg) is injected intraperitoneally into groups of 6 rats 0.5 hour after the administration of CRL 41 121. It is found that, at the strongest dose studied (32 mg/kg), CRL 41 121 causes a very substantial potentiation of the stereotypies induced by amphetamine.

VIII. INTERACTION WITH HALOPERIDOL

Groups of 6 rats receive 0.25 mg/kg of haloperidol by intraperitoneal administration 0.5 hour before the intraperitoneal administration of CRL 41 121 or amphetamine.

It is observed that haloperidol totally antagonizes the stereotypies induced by amphetamine, on the one hand, and CRL 41 121 at doses of 16 and 32 mg/kg, on the other.

VIII. INTERACTION WITH OXOTREMORINE

CRL 41 121 is administered to groups of 6 mice 0.5 hour before the intraperitoneal injection of 0.5 mg/kg of oxotremorine.

(1°) Action on the temperature

As from a dose of 4 mg/kg, CRL 41 121 opposes the hypothermic effect of oxotremorine.

(2°) Action on the trembling

At the strongest dose studied (64 mg/kg), CRL 41 121 slightly reduces the intensity of the trembling due to oxotremorine.

(3°) Action on the peripheral cholinergic symptoms

CRL 41 121 does not modify the signs of peripheral cholinergic stimulation produced by oxotremorine in mice (salivation, lacrimation, defecation).

IX. ACTION ON THE FOUR PLATE TEST, TRACTION AND ELECTRIC SHOCK

The test is performed on groups of 10 mice 0.5 hour after the administration of CRL 41 121.

It is observed that, at doses of 16 mg/kg and 64 mg/kg, CRL 41 121 causes a significant increase in the number of punished passes, that it does not cause motor incoordination and that, at a high dose (64 mg/kg), it opposes the convulsant effect of electric shock.

X. ACTION ON THE SPONTANEOUS MOTILITY

Half an hour after they have received CRL 41 121, the mice (6 per dose, 12 control animals) are placed in an actimeter, where their motility is recorded for 30 minutes. It is found that, as from a dose of 4 mg/kg, CRL 41 121 causes a substantial increase in the spontaneous motor activity of the mice.

XI. ACTION ON THE INTERGROUP AGGRESSIVENESS

After they have stayed for 3 weeks in the two halves of a cage divided by an opaque partition, groups of 3 mice receive CRL 41 121. Half an hour later, the two groups from the same cage are brought together by removal of the partition, and the number of fights which occur in 10 minutes is noted.

It is observed that, in contrast to the amphetamines, CRL 41 121 does not modify the intergroup aggressiveness, whether the dose used is an exciting dose (64 mg/kg) or a non-exciting dose (1 mg/kg).

XII. ACTION TOWARDS SOME FORMS OF BEHAVIOR PERTURBED BY VARIOUS AGENTS (1°) Motility reduced by habituation to the enclosure After they have stayed in the actimeters for 18 hours, the mice (6 per dose, 12 control animals) receive CRL 41 121. They are immediately returned to their respective enclosures and, half an hour later, their motility is recorded for 30 minutes.

It is noted that, as from a dose of 1 mg/kg, CRL 41 121 causes a resumption in the activity of mice accustomed to their enclosure.

(2°) Motility reduced by hypoxic aggression

Half an hour after they have received CRL 41 121, the mice (10 per dose, 20 control animals) are subjected to acute hypobaric anioxia [pressure reduction of 600 mm Hg (i.e. about $8 \times 10^4$ Pa) in 90 seconds, followed by release of vacuum in 45 seconds] and are then placed in an actimeter, where their motility is recorded for 10 minutes.

It is found that, at the strongest doses studied (16 mg/kg and 64 mg/kg), CRL 41 121 causes an improvement in the motor recovery of mice whose activity has been depressed following a brief period in a reduced-pressure enclosure.

(3°) Asphyxiant anoxia

Groups of 10 mice receive CRL 41 121 half an hour before the intraperitoneal administration of 32 mg/kg of gallamine triiodoethylate (reference curarizing agent).

CRL 41 121 does not change the time taken for convulsions and death to occur following asphyxiant anoxia caused by a curarizing agent.

XIII. INTERACTION WITH BARBITAL

Half an hour after the administration of CRL 41 121, groups of 10 mice receive an intraperitoneal injection of barbital (220 mg/kg).

As from a dose of 4 mg/kg, CRL 41 121 reduces the duration of the sleep induced by barbital. At the strongest dose studied (64 mg/kg), CRL 41 121 suppresses the effect of barbital.

XIV. ACTION OF THE "BEHAVIORAL DESPAIR"

Half an hour after they have received CRL 41 121, groups of 6 mice are placed in a beaker filled with water to a height of 6 cm. The total period of immobility between the 2nd and 6nd minutes following immersion is noted.

It is observed that, at doses of 16 mg/kg and 64 mg/kg, CRL 41 121 distinctly reduces the period of immobility due to "despair". This effect is still present at 4 mg/kg.

XV. INVESTIGATION OF A PARTICULAR TOXICITY IN GROUPED MICE

Immediately after the administration of CRL 41 121, groups of 10 mice are placed in small cages. The number of dead animals is noted every hour for 4 hours and after 24 hours. The toxicity of CRL 41 121 is determined under the same conditions with one mouse per cage. It is found that CRL 41 121 is no more toxic to isolated mice than to grouped mice.

XVI. INTERACTION WITH α-METHYLTYROSINE

Groups of 6 rats receive 128 mg/kg of α-methyltyrosine by intraperitoneal administration 2.5 hours before the intraperitoneal injection of CRL 41 121 or amphetamine.

It is observed that α-methyltyrosine (i) almost totally prevents the appearance of the stereotypies induced by amphetamine, but (ii) causes a decrease in the intensity and especially in the duration of the stereotypies induced by CRL 41 121 (at doses of 16 and 32 mg/kg), without however suppressing the said stereotypies.

XVII. INTERACTION WITH RESERPINE (1°) In mice

Four hours after the intraperitoneal injection of 2.5 mg/kg of reserpine, groups of 6 mice receive CRL 41 121. It is observed that, at doses of 4 mg/kg, 16 mg/kg and 64 mg/kg, CRL 41 121 opposes the hypothermia induced by reserpine; the ptosis is antagonized only at the strongest dose studied (64 mg/kg).

(2°) In rats

Groups of 6 rats receive an intraperitoneal injection of 4 mg/kg of reserpine either 4 hours (T −4 h) or 24 hours (T −24 h) before the intraperitoneal administration of CRL 41 121 (at doses of 16 and 32 mg/kg) or methylphenidate (i.e. methyl α-phenyl-2-piperidineacetate).

It is observed that the stereotype movements induced either by CRL 41 121 or by methylphenidate are practically suppressed by the prior administration (T −4 h) of reserpine.

On the other hand, the prior administration (T −24 h) of reserpine moderately reduces the intensity and more distinctly reduces the duration of the stereotypies caused by CRL 41 121 on the one hand and methylphenidate on the other.

XVIII. INTERACTION WITH THE ASSOCIATION RESERPINE+α-METHYLTYROSINE

Groups of 6 rats receive CRL 41 121 or methylphenidate by intraperitoneal administration 24 hours (T =24 h) after the intraperitoneal administration of 4 mg/kg of reserpine and 2.5 hours (T −2.5 h) after the intraperitoneal administration of 128 mg/kg of α-methyltyrosine.

It is found that the combined administration of reserpine (T =24 h) and α-methyltyrosine (T −2.5 h) prevents the appearance of the stereotype movements induced by CRL 41 121 (at doses of 16 and 32 mg/kg) on the one hand and methylphenidate on the other.

XIX. CONCLUSIONS

The neuropsychopharmacological tests summarized above show the CRL 41 121, administered intraperitoneally, has both antidepressant effects and stimulant effects. Furthermore, it is noted that CRL 41 121 exhibits effects which can be associated with a peripheral α-adrenergic stimulation (effects represented by antagonism of the ptosis induced by reserpine, antagonism of the trembling induced by oxotremorine, and mydriasis—however, it is observed that the animals exhibit neither piloerection nor thick salivation).

The blocking by haloperidol of the stereotypies induced by CRL 41 121 implies that the said stereotypies probably result from stimulation of a postsynaptic dopaminergic receptor. It seems that a direct action of CRL 41 121 on this receptor has to be excluded because manipulations of the pre-synaptic dopaminergic system [for example reserpine (T −4 h) or reserpine (T −24 h)+α-methyltyrosine (T −2.5 h) in rats] are capable of preventing the appearance of these stereotypies. Moreover, since α-methyltyrosine used on its own does not totally inhibit the effects of CRL 41 121 which cause stereotypies, whereas it suppresses the stereotypies induced by amphetamine (resulting in inhibition of catecholamine synthesis), it is assumed that, in the dopaminergic system, CRL 41 121 would release a small amount of newly synthesized dopamine (a phenomenon represented by the incomplete inhibition by α-methyltyrosine of the stereotypies induced in rats by CRL 41 121), and would inhibit the recapture of dopamine, resulting in the release of dopamine from a reserve pool.

In summary, the mechanism of action of CRL 41 121 is different from that of apomorphine and amphetamine but similar to that of methylphenidate or nomifensin.

XX. NEUROPSYCHOPHARMACOLOGICAL STUDY BY GASTRIC ADMINISTRATION

To complement the results mentioned above, additional tests were undertaken which involved the gastric administration of CRL 41 121, in solution in distilled water, in a volume of 20 ml/kg to male mice.

(1°) Action on the spontaneous motility

Following the protocol described in item X above, it is found that, as from a dose of 8 mg/kg, CRL 41 121 causes a great and statistically significant increase in the motor activity of mice. The effect increases with the dose and the hypermotility becomes very substantial at a dose of 128 mg/kg.

(2°) Interaction with barbital

Following the protocol described in item XIII above, it is found that, as from a dose of 8 mg/kg, CRL 41 121 reduces the duration of the sleep induced by barbital. The maximum effect is obtained at doses of 32 and 128 mg/kg.

(3°) Interaction with apomorphine

Groups of 12 mice receive CRL 41 121 half an hour before the subcutaneous injection of 16 mg/kg of apomorphine. It is observed that, at the strongest doses used (32 and 128 mg/kg), CRL 41 121 distinctly antagonizes the hypothermic action of apomorphine without modifying the righting behavior and the stereotypies.

Taken overall, the neuropsychopharmacological tests carried out by gastric administration show that the stimulant-type and/or arousing-type effects of CRL 41 121 appear at doses greater than and equal to 8 mg/kg.

On the other hand, antidepressant-type effects only appear at doses of 32 mg/kg and above.

The dose-dependent dissociation between the stimulant-type and/or arousing-type effects and the antidepressant-type effects, observed after gastric administration of CRL 41 121, is comparable to that obtained after intraperitoneal administration.

In clinical trials, good results have been obtained from the oral administration of CRL 41 121 (in the form of tablets or gelatine capsules) as an antidepressant in the treatment of depressions and depressive states.

What is claimed is:

1. A 1-(aminophenyl)-2-aminoethanone derivative selected from the group consisting of:
   (i) 1-(aminophenyl)-2-(alkylamino)ethanones of the formula:

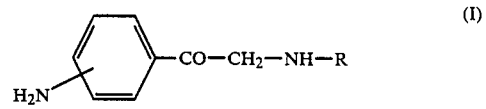

in which R is $CH(CH_3)_2$ or $C(CH_3)_3$; and
   (ii) addition salts thereof.

2. A derivative according to claim 1, wherein the $NH_2$ group is in the para position on the phenyl nucleus, relative to the carbonyl group.

3. A derivative according to claim 1, wherein R is $CH(CH_3)_2$.

4. 1-(4-Aminophenyl)-2-isopropylaminoethanone and addition salts thereof.

5. A therapeutic composition comprising, in association with a physiologically acceptable excipient, a pharmaceutically effective quantity of a compound selected from the group consisting of (i) 1-(aminophenyl)-2-(alkylamino)ethanones of the formula I according to claim 1, and (ii) non-toxic addition salts thereof.

6. A therapeutic composition according to claim 5, comprising a pharmaceutically effective quantity of 1-(4-aminophenyl)-2-isopropylaminoethanone or a non-toxic addition salt thereof.

7. A method for the treatment of depression, which comprises administering, to a patient in need of such a treatment, a pharmaceutically effective quantity of a 1-(aminophenyl)-2-aminoethanone derivative of the formula I according to claim 1, or one of its non-toxic addition salts.

8. A method for treatment of depression which comprises administering to a patient in need of such a treatment, a pharmaceutically effective quantity of 1-(4-aminophenyl)-2-isopropylaminoethanone or a non-toxic addition salt thereof.

* * * * *

UNITED STATES PATENT AND TRADEMARK OFFICE
CERTIFICATE OF CORRECTION

PATENT NO. : 4,816,489
DATED : March 28, 1989
INVENTOR(S) : Louis Lafon

It is certified that error appears in the above-identified patent and that said Letters Patent is hereby corrected as shown below:

On The Title Page,

Add the following:

-- [30] FOREIGN APPLICATION PRIORITY DATA

Aug. 20, 1984 [FR] France...84 12966 --.

Signed and Sealed this

Fifth Day of December, 1989

*Attest:*

JEFFREY M. SAMUELS

*Attesting Officer*      *Acting Commissioner of Patents and Trademarks*